(12) United States Patent
Weber

(10) Patent No.: US 11,791,043 B2
(45) Date of Patent: Oct. 17, 2023

(54) METHODS OF PROGNOSING EARLY STAGE BREAST LESIONS

(71) Applicant: University of Cincinnati, Cincinnati, OH (US)

(72) Inventor: Georg F. Weber, Cincinnati, OH (US)

(73) Assignee: University of Cincinnati, Cincinnati, OH (US)

(*) Notice: Subject to any disclaimer, the term of this patent is extended or adjusted under 35 U.S.C. 154(b) by 693 days.

(21) Appl. No.: 16/644,239

(22) PCT Filed: Sep. 6, 2018

(86) PCT No.: PCT/US2018/049684
§ 371 (c)(1),
(2) Date: Mar. 4, 2020

(87) PCT Pub. No.: WO2019/051041
PCT Pub. Date: Mar. 14, 2019

(65) Prior Publication Data
US 2020/0271652 A1    Aug. 27, 2020

Related U.S. Application Data

(60) Provisional application No. 62/554,712, filed on Sep. 6, 2017.

(51) Int. Cl.
*G16H 50/20*    (2018.01)

(52) U.S. Cl.
CPC ......... *G16H 50/20* (2018.01); *G01N 2333/52* (2013.01); *G01N 2800/50* (2013.01); *G01N 2800/52* (2013.01)

(58) Field of Classification Search
CPC ............... G16H 50/20; G01N 2333/52; G01N 2800/50; G01N 2800/52; G01N 33/57415;
(Continued)

(56) References Cited

U.S. PATENT DOCUMENTS

2009/0061436 A1* 3/2009 Weber ............... G01N 33/57484
435/375
2010/0209928 A1* 8/2010 Mirza .................... C07K 16/18
435/7.1
(Continued)

OTHER PUBLICATIONS

Extended European Search Report pertaining to corresponding European Patent Application No. 18854610.5 dated May 11, 2021.
(Continued)

*Primary Examiner* — Gregory D. Moseley
(74) *Attorney, Agent, or Firm* — DINSMORE & SHOHL LLP

(57) ABSTRACT

A method is provided for prognosing a risk in a patient diagnosed with a premalignant lesion of the breast of the lesion progressing to breast cancer, the method comprising: providing a tissue sample of the premalignant lesion; detecting one or more variants of Osteopontin (OPN) selected from OPN-a, OPN-b and OPN-c in the sample; and prognosing an elevated risk of the lesion progressing to breast cancer if OPN-b and/or OPN-c is detected and/or OPN-a is elevated above normal levels in the tissue sample. Methods of assessing risk of death from breast cancer, methods of treatment, and kits for prognosis are also provided herein.

14 Claims, 6 Drawing Sheets

Specification includes a Sequence Listing.

(58) Field of Classification Search
CPC .. G01N 33/53; G01N 33/574; G01N 33/6893; C07K 16/24; C07K 14/52
See application file for complete search history.

(56) References Cited

U.S. PATENT DOCUMENTS

| | | |
|---|---|---|
| 2010/0291125 A1 | 11/2010 | Winslow et al. |
| 2011/0165697 A1 | 7/2011 | Liaw et al. |
| 2018/0200206 A1* | 7/2018 | Quay ................. A61P 35/00 |
| 2019/0125735 A1* | 5/2019 | Mani ................. A61K 31/506 |

OTHER PUBLICATIONS

Mirkin, et al., "Selective estrogen receptor modulators (SERMs): A review of clinical data", Maturitas, 2014, 52-57, vol. 80 No 1.

Cole, et al., "Biological characteristics of premalignant breast disease", Cancer Biomark, 2010, 177-192.

Santisteban, et al., "Ki67: a time-varying biomarker of risk of breast cancer in atypical hyperplasia", Breast Cancer Research and Treatment, 2009, 431-437, vol. 121 No. 2.

Walaszek, et al., "Breast cancer risk in premalignant lesions: osteopontin splice variants indicate prognosis", British Journal of Cancer, 2018, 1259-1266, vol. 119 No. 10.

International Search Report & Written Opinion to corresponding PCT Application No. PCT/US2018/049684 dated Nov. 19, 2018.

Marco Antonio Briones-Orta et al., Osteopontin splice variants and polymorphisms in cancer progression and prognosis; Biochimica et Biophysica Acta Rev Cancer, 1868: 93-108. (2017).

K. Zduniak et al., Nuclear osteopontin-c is a prognostic breast cancer marker; British Journal of Cancer (2015) 112: 729-738.

K. Zduniak et al., Osteopontin splice variants are differential predictors of breast cancer treatment responses; BMC Cancer (2016) 16:441.

* cited by examiner

SEQUENCE LISTING

```
<160> NUMBER OF SEQ ID NOS: 8

<210> SEQ ID NO 1
<211> LENGTH: 314
<212> TYPE: PRT
<213> ORGANISM: Homo sapiens
<220> FEATURE:
<221> NAME/KEY: MISC_FEATURE
<223> OTHER INFORMATION: OPN-a

<400> SEQUENCE: 1

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285
```

```
Pro Lys Ser Lys Glu Glu Asp Lys His Leu Lys Phe Arg Ile Ser His
        290                 295                 300

Glu Leu Asp Ser Ala Ser Ser Glu Val Asn
305                 310

<210> SEQ ID NO 2
<211> LENGTH: 300
<212> TYPE: PRT
<213> ORGANISM: Homo sapiens
<220> FEATURE:
<221> NAME/KEY: MISC_FEATURE
<223> OTHER INFORMATION: OPN-b

<400> SEQUENCE: 2

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
            260                 265                 270

Val Asp Pro Lys Ser Lys Glu Glu Asp Lys His Leu Lys Phe Arg Ile
        275                 280                 285

Ser His Glu Leu Asp Ser Ala Ser Ser Glu Val Asn
    290                 295                 300

<210> SEQ ID NO 3
<211> LENGTH: 287
<212> TYPE: PRT
<213> ORGANISM: Homo sapiens
```

<220> FEATURE:
<221> NAME/KEY: MISC_FEATURE
<223> OTHER INFORMATION: OPN-c

<400> SEQUENCE: 3

```
Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Asn
            20                  25                  30

Ala Val Ser Ser Glu Glu Thr Asn Asp Phe Lys Gln Glu Thr Leu Pro
        35                  40                  45

Ser Lys Ser Asn Glu Ser His Asp His Met Asp Asp Met Asp Asp Glu
50                  55                  60

Asp Asp Asp Asp His Val Asp Ser Gln Asp Ser Ile Asp Ser Asn Asp
65                      70                  75                  80

Ser Asp Asp Val Asp Asp Thr Asp Asp Ser His Gln Ser Asp Glu Ser
                85                  90                  95

His His Ser Asp Glu Ser Asp Glu Leu Val Thr Asp Phe Pro Thr Asp
            100                 105                 110

Leu Pro Ala Thr Glu Val Phe Thr Pro Val Val Pro Thr Val Asp Thr
            115                 120                 125

Tyr Asp Gly Arg Gly Asp Ser Val Val Tyr Gly Leu Arg Ser Lys Ser
130                 135                 140

Lys Lys Phe Arg Arg Pro Asp Ile Gln Tyr Pro Asp Ala Thr Asp Glu
145                 150                 155                 160

Asp Ile Thr Ser His Met Glu Ser Glu Glu Leu Asn Gly Ala Tyr Lys
                165                 170                 175

Ala Ile Pro Val Ala Gln Asp Leu Asn Ala Pro Ser Asp Trp Asp Ser
            180                 185                 190

Arg Gly Lys Asp Ser Tyr Glu Thr Ser Gln Leu Asp Asp Gln Ser Ala
        195                 200                 205

Glu Thr His Ser His Lys Gln Ser Arg Leu Tyr Lys Arg Lys Ala Asn
    210                 215                 220

Asp Glu Ser Asn Glu His Ser Asp Val Ile Asp Ser Gln Glu Leu Ser
225                 230                 235                 240

Lys Val Ser Arg Glu Phe His Ser His Glu Phe His Ser His Glu Asp
                245                 250                 255

Met Leu Val Val Asp Pro Lys Ser Lys Glu Glu Asp Lys His Leu Lys
            260                 265                 270

Phe Arg Ile Ser His Glu Leu Asp Ser Ala Ser Ser Glu Val Asn
        275                 280                 285
```

<210> SEQ ID NO 4
<211> LENGTH: 1641
<212> TYPE: DNA
<213> ORGANISM: Homo sapiens
<220> FEATURE:
<221> NAME/KEY: misc_feature
<223> OTHER INFORMATION: OPN-a

<400> SEQUENCE: 4

```
ctccctgtgt tggtggagga tgtctgcagc agcatttaaa ttctgggagg gcttggttgt    60
cagcagcagc aggaggaggc agagcacagc atcgtcggga ccagactcgt ctcaggccag   120
ttgcagcctt tcagccaaa cgccgaccaa ggaaaactca ctaccatgag aattgcagtg    180
atttgctttt gcctcctagg catcacctgt gccataccag ttaaacaggc tgattctgga   240
```

```
agttctgagg aaaagcagct ttacaacaaa tacccagatg ctgtggccac atggctaaac    300
cctgacccat ctcagaagca gaatctccta gccccacaga atgctgtgtc ctctgaagaa    360
accaatgact ttaaacaaga gacccttcca agtaagtcca acgaaagcca tgaccacatg    420
gatgatatgg atgatgaaga tgatgatgac catgtggaca gccaggactc cattgactcg    480
aacgactctg atgatgtaga tgacactgat gattctcacc agtctgatga gtctcaccat    540
tctgatgaat ctgatgaact ggtcactgat tttcccacgg acctgccagc aaccgaagtt    600
ttcactccag ttgtccccac agtagacaca tatgatggcc gaggtgatag tgtggtttat    660
ggactgaggt caaaatctaa gaagtttcgc agacctgaca tccagtaccc tgatgctaca    720
gacgaggaca tcacctcaca catggaaagc gaggagttga atggtgcata caaggccatc    780
cccgttgccc aggacctgaa cgcgccttct gattgggaca gccgtgggaa ggacagttat    840
gaaacgagtc agctggatga ccagagtgct gaaacccaca gccacaagca gtccagatta    900
tataagcgga aagccaatga tgagagcaat gagcattccg atgtgattga tagtcaggaa    960
ctttccaaag tcagccgtga attccacagc catgaatttc acagccatga agatatgctg   1020
gttgtagacc ccaaaagtaa ggaagaagat aaacacctga atttcgtat ttctcatgaa    1080
ttagatagtg catcttctga ggtcaattaa aaggagaaaa aatacaattt ctcactttgc   1140
atttagtcaa aagaaaaaat gctttatagc aaaatgaaag agaacatgaa atgcttcttt   1200
ctcagtttat tggttgaatg tgtatctatt tgagtctgga ataactaat gtgtttgata    1260
attagtttag tttgtggctt catggaaact ccctgtaaac taaaagcttc agggttatgt   1320
ctatgttcat tctatagaag aaatgcaaac tatcactgta ttttaatatt tgttattctc   1380
tcatgaatag aaatttatgt agaagcaaac aaaatacttt tacccactta aaaagagaat   1440
ataacatttt atgtcactat aatctttgt ttttttaagtt agtgtatatt ttgttgtgat    1500
tatcttttg tggtgtgaat aaatctttta tcttgaatgt aataagaatt tggtggtgtc     1560
aattgcttat ttgttttccc acggttgtcc agcaattaat aaaacataac ctttttact    1620
gcctaaaaaa aaaaaaaaa a                                                1641

<210> SEQ ID NO 5
<211> LENGTH: 1641
<212> TYPE: DNA
<213> ORGANISM: Homo sapiens
<220> FEATURE:
<221> NAME/KEY: misc_feature
<223> OTHER INFORMATION: OPN-b

<400> SEQUENCE: 5
ctccctgtgt tggtggagga tgtctgcagc agcatttaaa ttctgggagg gcttggttgt     60
cagcagcagc aggaggaggc agagcacagc atcgtcggga ccagactcgt ctcaggccag   120
ttgcagcctt ctcagccaaa cgccgaccaa ggaaaactca ctaccatgag aattgcagtg   180
atttgctttt gcctcctagg catcacctgt gccataccag ttaaacaggc tgattctgga   240
agttctgagg aaaagcagct ttacaacaaa tacccagatg ctgtggccac atggctaaac   300
cctgacccat ctcagaagca gaatctccta gccccacaga atgctgtgtc ctctgaagaa   360
accaatgact ttaaacaaga gacccttcca agtaagtcca acgaaagcca tgaccacatg   420
gatgatatgg atgatgaaga tgatgatgac catgtggaca gccaggactc cattgactcg   480
aacgactctg atgatgtaga tgacactgat gattctcacc agtctgatga gtctcaccat   540
tctgatgaat ctgatgaact ggtcactgat tttcccacgg acctgccagc aaccgaagtt   600
```

```
ttcactccag ttgtccccac agtagacaca tatgatggcc gaggtgatag tgtggtttat    660
ggactgaggt caaaatctaa gaagtttcgc agacctgaca tccagtaccc tgatgctaca    720
gacgaggaca tcacctcaca catggaaagc gaggagttga atggtgcata caaggccatc    780
cccgttgccc aggacctgaa cgcgccttct gattgggaca gccgtgggaa ggacagttat    840
gaaacgagtc agctggatga ccagagtgct gaaacccaca gccacaagca gtccagatta    900
tataagcgga agccaatgat gagagcaatg agcattccga tgtgattgaa tagtcaggaa    960
ctttccaaag tcagccgtga attccacagc catgaatttc acagccatga agatatgctg   1020
gttgtagacc ccaaaagtaa ggaagaagat aaacacctga aatttcgtat ttctcatgaa   1080
ttagatagtg catcttctga ggtcaattaa aaggagaaaa aatacaattt ctcactttgc   1140
atttagtcaa aagaaaaaat gcttatagc aaaatgaaag agaacatgaa atgcttcttt   1200
ctcagtttat tggttgaatg tgtatctatt tgagtctgga ataactaat gtgtttgata    1260 attagtttag tttgtggctt catggaaact ccctgtaaac taaaagcttc agggttatgt   1320
ctatgttcat tctatagaag aaatgcaaac tatcactgta ttttaatatt tgttattctc   1380
tcatgaatag aaatttatgt agaagcaaac aaaatacttt tacccactta aaaagagaat   1440
ataacatttt atgtcactat aatcttttgt tttttaagtt agtgtatatt tgttgtgat    1500 tatcttttg tggtgtgaat aaatcttta tcttgaatgt aataagaatt tggtggtgtc   1560
aattgcttat ttgttttccc acggttgtcc agcaattaat aaaacataac ctttttact   1620 gcctaaaaaa aaaaaaaaa a                                              1641

<210> SEQ ID NO 6
<211> LENGTH: 1560
<212> TYPE: DNA
<213> ORGANISM: Homo sapiens
<220> FEATURE:
<221> NAME/KEY: misc_feature
<223> OTHER INFORMATION: OPN-c

<400> SEQUENCE: 6
ctccctgtgt tggtggagga tgtctgcagc agcatttaaa ttctgggagg gcttggttgt     60
cagcagcagc aggaggaggc agagcacagc atcgtcggga ccagactcgt tcaggccag    120 ttgcagcctt tcagccaaa cgccgaccaa ggaaaactca ctaccatgag aattgcagtg    180
atttgctttt gcctcctagg catcacctgt gccataccag ttaaacaggc tgattctgga    240
agttctgagg aaaagcagaa tgctgtgtcc tctgaagaaa ccaatgactt taaacaagag    300
acccttccaa gtaagtccaa cgaaagccat gaccacatgg atgatatgga tgatgaagat    360
gatgatgacc atgtggacag ccaggactcc attgactcga cgactctga tgatgtagat    420 gacactgatg attctcacca gtctgatgag tctcaccatt ctgatgaatc tgatgaactg    480
gtcactgatt ttcccacgga cctgccagca accgaagttt tcactccagt tgtccccaca    540
gtagacacat atgatggccg aggtgatagt gtggtttatg gactgaggtc aaaatctaag    600
aagtttcgca gacctgacat ccagtaccct gatgctacag acgaggacat cacctcacac    660
atggaaagcg aggagttgaa tggtgcatac aaggccatcc ccgttgccca ggacctgaac    720
gcgccttctg attgggacag ccgtgggaag gacagttatg aaacgagtca gctggatgac    780
cagagtgctg aaacccacag ccacaagcag tccagattat ataagcggaa agccaatgat    840
gagagcaatg agcattccga tgtgattgat agtcaggaac tttccaaagt cagccgtgaa    900
ttccacagcc atgaatttca cagccatgaa gatatgctgg ttgtagaccc caaaagtaag    960
```

```
gaagaagata aacacctgaa atttcgtatt tctcatgaat tagatagtgc atcttctgag    1020
gtcaattaaa aggagaaaaa atacaatttc tcactttgca tttagtcaaa agaaaaaatg    1080
ctttatagca aaatgaaaga gaacatgaaa tgcttctttc tcagtttatt ggttgaatgt    1140
gtatctattt gagtctggaa ataactaatg tgtttgataa ttagtttagt ttgtggcttc    1200
atggaaactc cctgtaaact aaaagcttca gggttatgtc tatgttcatt ctatagaaga    1260
aatgcaaact atcactgtat tttaatattt gttattctct catgaataga aatttatgta    1320
gaagcaaaca aaatactttt acccacttaa aaagagaata taacatttta tgtcactata    1380
atcttttgtt ttttaagtta gtgtatattt tgttgtgatt atctttttgt ggtgtgaata    1440 aatctttat cttgaatgta ataagaattt ggtggtgtca attgcttatt tgttttccca    1500
cggttgtcca gcaattaata aaacataacc ttttttactg cctaaaaaaa aaaaaaaaaa    1560
```

```
<210> SEQ ID NO 7
<211> LENGTH: 9
<212> TYPE: PRT
<213> ORGANISM: Artificial Sequence
<220> FEATURE:
<223> OTHER INFORMATION: Synthetic protein sequence

<400> SEQUENCE: 7

Ser Glu Glu Lys Gln Asn Ala Val Ser
1               5

<210> SEQ ID NO 8
<211> LENGTH: 27
<212> TYPE: PRT
<213> ORGANISM: Artificial Sequence
<220> FEATURE:
<223> OTHER INFORMATION: Synthetic protein sequence

<400> SEQUENCE: 8

Leu Tyr Asn Lys Tyr Pro Asp Ala Val Ala Thr Trp Leu Asn Pro Asp
1               5                   10                  15

Pro Ser Gln Lys Gln Asn Leu Leu Ala Pro Asn
            20                  25
```

METHODS OF PROGNOSING EARLY STAGE BREAST LESIONS

CROSS REFERENCE TO RELATED APPLICATIONS

This application is a § 371 U.S. National Stage Application of International Application No. PCT/US2018/049684 filed Sep. 6, 2018, and claims priority to U.S. Provisional Application No. 62/554,712 filed Sep. 6, 2017, the contents of which are incorporated herein by reference.

FIELD

The invention relates to methods of determining or predicting breast cancer using biomarkers expressed or absent in premalignant lesions.

BACKGROUND

Women that are found to have preinvasive lesions of the breast historically are faced with only three options following their diagnosis: observation; chemoprevention; or surgery (e.g., lumpectomy or mastectomy). There are, unfortunately, no predictors for progression risk that are specific to the woman's diagnosis to guide the decision regarding which path to follow. Distinguishing high-risk patients from low-risk patients would improve the prognosis of high-risk patients (through early decisive intervention) and spare unnecessary treatment for the low-risk patients (through continued observation).

Currently available diagnostic techniques in breast cancer prevention involve a biopsy, where samples of tissue are taken to confirm or eliminate the presence of transformed cells by histopathological examination. These processes lack indicators for the detection of invasive potential, may understate the disease identified, and the early stages of breast transformation (atypias) are difficult to differentiate from benign growths (hyperplasias) on one end of the spectrum and invasive carcinomas in situ (CIS) on the other end. Furthermore, the inspection of tumor margins to assess invasiveness is unreliable and it requires step sections through the entire biopsy material. Microinvasion is typically identified at surgical biopsy, as core needle tissue cannot enable this distinction.

Hence, there is an intense need for dependable biomarkers. The lack of reliable molecular indicators for breast cancer progression, however, has led to efforts to use increasingly complex readouts. Multiple tumor markers, including HER2 amplification/over-expression, cathepsin D, and uPAR, have been considered for prognostication and therapy decisions of breast cancer in a Tumor Marker Utility Grading System (Hayes et al., *Breast Cancer Res. Treat.* 52:305-19, 1998). A gene prognosis profile of 70 genes, developed at the Netherlands Cancer Institute, has been characterized as a good predictor of outcome (van de Vijver et al., *N. Engl. J. Med.* 347:1999-2009, 2002). The likelihood of distant recurrence in breast cancer patients, who have estrogen receptor positive tumors and no involved lymph nodes, can be defined with a panel of 21 gene products, amplified by RT-PCR from paraffin blocks, and correlated with the likelihood of distant recurrence (Paik et al., *N. Engl. J. Med.* 351:2817-2826, 2004).

As such, there exists a need for improved molecular biomarker assays and processes for prognosing breast tumor invasiveness at an early stage of diagnosis such as through effective analyses of premalignant breast lesions.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

In one embodiment, a method is provided for prognosing a risk in a patient diagnosed with a premalignant lesion of the breast, of the lesion progressing to breast cancer, the method comprising: providing a tissue sample of the premalignant lesion; detecting one or more variants of Osteopontin (OPN) selected from OPN-a, OPN-b and OPN-c in the sample; and prognosing an elevated risk of the lesion progressing to breast cancer if OPN-b and/or OPN-c is detected and/or OPN-a is elevated above normal levels in the tissue sample.

In another embodiment, a method is provided of assessing risk of death from breast cancer in a patient diagnosed with a premalignant lesion of the breast, the method comprising: providing a sample of the lesion and immunohistochemically detecting OPN-a, OPN-b and/or OPN-c in the sample by detecting selective anti-OPN-c and anti-OPN-a/b stains; and assessing the risk of death as elevated if OPN-c is detected.

In another embodiment, a method is provided of treating a patient diagnosed with a premalignant lesion of the breast, the method comprising: prognosing a risk of the lesion progressing to breast cancer by providing a tissue specimen of the premalignant lesion, detecting one or more variants of Osteopontin (OPN) selected from OPN-a, OPN-b and OPN-c in the sample, and prognosing an elevated risk of the lesion progressing to breast cancer if OPN-c is detected in the tissue sample; and treating the patient by administering chemoprevention therapy or surgery if an elevated risk is prognosed, or subjecting the patient to continued observation without chemoprevention or surgery if an elevated risk is not prognosed.

In a further embodiment, a kit for the prognosis of premalignant breast cancer lesions is provided, the kit comprising: an antibody selected for OPN-c; an antibody selective for OPN exon 4; and reagents for conducing an immunohistochemical analysis of a sample of a premalignant breast cancer lesion.

SEQUENCE LISTING

Figure 1:
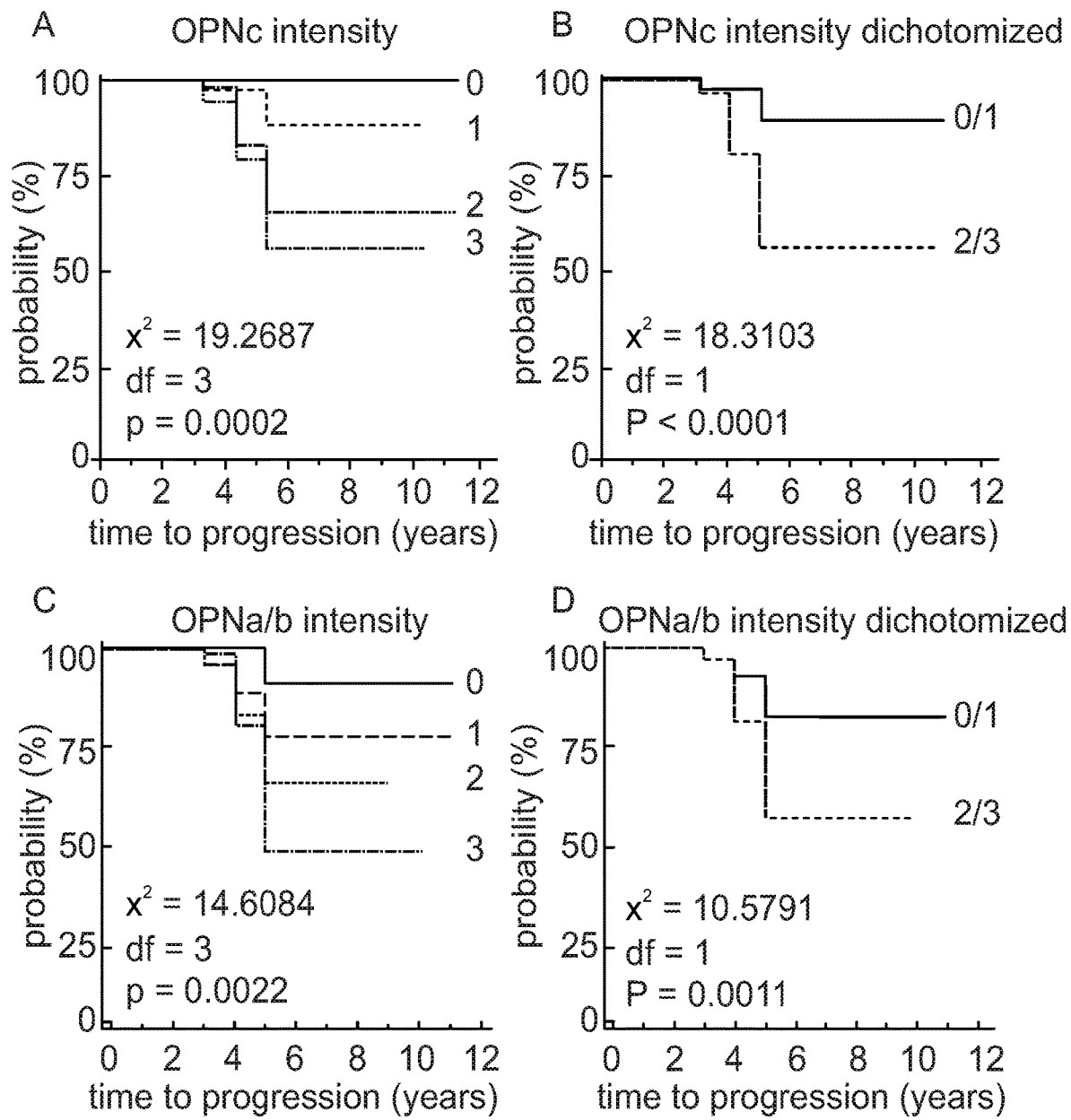
FIG. 1 illustrates OPN splice variants are indicators for prognosis. Kaplan-Meier curves for the risk of progression over time. The x-axis shows the time of follow-up in years, the y-axis displays the probability of remaining recurrence-free cases in percent of the total number. The measured variables in A,C are categorical. The variables in B,D are dichotomized. The $\chi^2$ statistic is inserted into the lower left corner of the graphs, df=degrees of freedom. A) OPN-c intensity. B) OPN-c intensity dichotomized. C) OPN exon 4 intensity. D) OPN exon 4 intensity dichotomized.

Applicant hereby incorporates by reference a CRF sequence listing submitted herewith having a file name 10738-652_Sequence_Listing.txt created on Sep. 5, 2018.

The nucleic and amino acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing:

SEQ ID NO: 1 represents a peptide sequence of OPN-a.
SEQ ID NO: 2 represents a peptide sequence of OPN-b.
SEQ ID NO: 3 represents a peptide sequence of OPN-c.
SEQ ID NO: 4 represents a coding nucleic acid sequence of OPN-a.
SEQ ID NO: 5 represents a coding nucleic acid sequence of OPN-b.
SEQ ID NO: 6 represents a coding nucleic acid sequence of OPN-c.
SEQ ID NO: 7 represents an epitope found specifically in OPN-c.
SEQ ID NO: 8 represents an epitope found specifically in OPN-a and OPN-b.

DETAILED DESCRIPTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The processes and kits as described herein have utility as a predictor of elevated risk of a premalignant lesion of the breast progressing to breast cancer in a subject. As such, provided are processes of prognosing a risk of a premalignant lesion of the breast in a patient progressing to breast cancer. The invention identifies and categorizes expression of one or more of the gene products of cytokine Osteopontin (OPN, Spp1). OPN in broad sense has been extensively studied as a metastasis gene representing the most abundantly secreted phospho-protein in breast and other cancers and is believed to support invasive behavior. As such, OPN is a biomarker for breast cancer aggressiveness and for breast cancer prognosis where the abundance of Osteopontin correlates negatively with survival. In older studies, pan-Osteopontin (total Osteopontin, typically covering all variant forms) was measured. (Weber G F, et al., *Brit J Cancer* 2010; 103:861-869, Weber G F, et al., *Oncol Reports* 2011; 25:433-441) It was found that pan-Osteopontin correlated with premalignant progression in breast and other transformations (Weber G F, et al., *Brit J Cancer* 2010; 103:861-869).

The gene product of OPN, however, is subject to alternative splicing selectively in cancer, which deletes exon 4 (27 amino acids) to generate Osteopontin-c (OPN-c), or exon 5 (to generate Osteopontin-b (OPN-b)) from the unspliced form (called Osteopontin-a (OPN-a)). OPN-c lacks exon 4 in the $NH_2$-terminal region of the mature sequence. OPN-c lacks the transglutaminase reactive domain (Gly-X-Gly) which can mediate covalent homodimer cross-linking as well as heterodimer formation to other matrix components (such as fibronectin). This description provides processes that examine the levels by intensity or percent positivity of histological samples of premalignant lesions of the breast to determine whether or prognosticate if the lesions will become breast cancer in the subject.

Processes as provided herein include prognosing risk of progressing to breast cancer in a subject or assessing risk of death in a subject as a relation between the extent of expression of one of more OPN variants alone or optionally in conjunction with a measure of pathology score, detection intensity, percent positivity, or risk category. Processes in some aspects as provided herein include providing a tissue sample of a premalignant breast lesion from a subject, detecting one or more variants of Osteopontin (OPN) in the sample where the variants are OPN-a, OPN-b or OPN-c, and prognosing an elevated risk of the lesion progressing to breast cancer if OPN-b and/or OPN-c is detected and/or OPN-a is elevated above normal levels in the tissue sample. It was found specifically, that elevated risk of the lesion progressing to breast cancer was observed particularly with levels of OPN-c that could be categorized as high independent of the type of lesion found in the subject. In addition, the presence of high levels OPN-b/a expression, particularly in high risk lesions correlated with increased chance of breast cancer in subjects.

As used herein a "subject" is a mammal. Optionally, a subject is a human or non-human primate. Optionally, a subject is a dog, cat, equine, sheep, bovine, rabbit, pig, or murine.

As used herein, the term "tissue sample" is defined as sample obtained from a biological organism, a tissue, cell, or any medium suitable for mimicking biological conditions, or from the environment. Illustratively, a tissue sample includes breast tissue, such as that obtained during a needle biopsy, lumpectomy, or mastectomy. Samples, such as tissue samples, can be placed on microscope slides. In particular examples, samples are used directly, or can be manipulated prior to use, for example, by fixing (e.g., using formalin) or embedding (e.g., in plastic or paraffin). A sample is optionally a nucleic sample meaning that the sample includes material or is specifically selected to be derived from or target a nucleus. Optionally, a sample is a cytoplasmic sample meaning that the sample includes or is specifically selected to be derived from or target cytoplasm.

The term "breast cancer" as used herein includes any tumor of the breast, such as tumors of epithelial (carcinoma) or stromal (sarcoma) breast tissue. Exemplary in situ epithelial breast cancers include ductal carcinoma in situ (DCIS) and lobular carcinoma in situ (LCIS). LCIS is a tumor that consists of abnormal cells in the lining of a lobule. DCIS is made up of abnormal cells in the lining of a duct. Exemplary invasive breast carcinomas include carcinoma NOS (not otherwise specified), lobular carcinoma, tubular/cribriform carcinoma, mucinous (colloid) carcinoma, medullary carcinoma, papillary carcinoma, and metaplastic carcinoma. An exemplary breast sarcoma is phyllodes tumor.

A process as provided herein includes detecting the presence or absence of one or more variants of OPN. A variant of OPN may be OPN-a, OPN-b or OPN-c. The amino acid sequences of the OPN variants are known. An exemplary sequence of OPN-a in a human is MRIAVICFCLLGIT-CAIPVKQADSGSSEEKQLYNKYPDAVATWLNPDP-SQKQNLL APQNAVSSEETNDFKQETLPSKS-NESHDHMDDMDDEDDDDHVDSQDSIDSNDS DDVDDTDDSHQSDESHHSDESDELVTDFPTDL-PATEVFTPVVPTVDTYDGRGDS VVYGLRSK-SKKFRRPDIQYPDATDEDITSHMESEELN-GAYKAIPVAQDLNAPSD WDSRGKDSYETSQLDDQSAETHSHKQSRLYKR-KANDESNEHSDVIDSQELSKVS REFHSHEFHSHEDMLVVDPKSKEEDKHLKFR-ISHELDSASSEVN (SEQ ID NO: 1). An OPN-a sequence includes a wild-type (or native) sequence of SEQ ID NO: 1, as well as OPN-a variants (e.g., polymorphisms) expressed in breast cancer cells. In certain examples, OPN-a has at least 80% sequence identity, for example at least 85%, at least 90%, at least 95%, or at least 98% sequence identity to SEQ ID NO: 1.

An exemplary sequence of OPN-b in a human is MRIA-VICFCLLGITCAIPVKQADSGSSEEKQLYNKYPDA-VATWLNPDPSQKQNLL APQTLPSKS-NESHDHMDDMDDEDDDDHVDSQDSIDSNDSDDV-DDTDDSHQSDE SHHSDESDELVTDFPTDL-PATEVFTPVVPTVDTYDGRGDSVVYGLRSKSKKFRR PDIQYPDATDEDITSHMESEELN-GAYKAIPVAQDLNAPSDWDSRGKDSYETSQL DDQ-SAETHSHKQSRLYKRKANDESNEHSDVIDSQEL-SKVSREFHSHEFHSHEDM LVVDPKSKEEDKHLKFRISHELDSASSEVN (SEQ ID NO: 2). An OPN-b sequence includes a wild-type (or native) sequence of SEQ ID NO: 2, as well as OPN-b variants (e.g., polymorphisms) expressed in breast cancer cells. In certain examples, OPN-b has at least 80% sequence identity, for example at least 85%, at least 90%, at least 95%, or at least 98% sequence identity to SEQ ID NO: 2.

An exemplary sequence of OPN-c in a human is MRIA-VICFCLLGITCAIPVKQADSGSSEEKQNAVSSEETND-FKQETLPSKSNESHD HMDDMDDEDDD-DHVDSQDSIDSNDSDDVDDTDDSHQSDESHHSDE-SDELVTDF PTDLPATEVFTPVVPTVDTYDGRGDSV- VYGLRSKSKKFRRPDIQYPDATDEDITS HMESEELN-GAYKAIPVAQDLNAPSDWDSRGKDSYETSQLDDQ-SAETHSHKQSR LYKRKANDESNEHSDVIDSQELSKVS-REFHSHEFHSHEDMLVVDPKSKEEDKHL KFR-ISHELDSASSEVN (SEQ ID NO: 3). An OPN-c sequence includes a wild-type (or native) sequence of SEQ ID NO: 3, as well as OPN-c variants (e.g., polymorphisms) expressed in breast cancer cells. In certain examples, OPN-c has at least 80% sequence identity, for example at least 85%, at least 90%, at least 95%, or at least 98% sequence identity to SEQ ID NO: 3.

An exemplary coding nucleic acid sequence of human OPN-a is ctccctgtgttggtggaggatgtctgcagcagcatttaaattctgg-gagggcttggttgtcagcagcagcaggaggaggcagag cacag-catcgtcgggaccagactcgtctcaggccagttgcagccttctcagc-caaacgccgaccaaggaaaactcactaccat gagaattgcagtgatttgcttttgcctcctaggcatcacctgtgccataccagt-taaacaggctgattctggaagttctgaggaaaa gcagctttacaacaaataccca-gatgctgtggccacatggctaaacctgacc-catctcagaagcagaatctcctagccccaca gaatgctgtgtcctctgaagaaaccaatgactttaaacaagagacccttc-caagtaagtccaacgaaagccatgaccacatggat gatatggatgatgaagat-gatgatgaccatgtggacagccaggactccattgactcgaacgactctgat-gatgtagatgacactg atgattctcaccagtctgatgagtctcaccattctgatgaatctgatgaactggtcact-gattttcccacggacctgccagcaaccg aagttttcactccagttgtccc-cacagtagacacatatgatggccgaggtgatagtgtggtttatggactgaggt-caaaatctaag aagtttcgcagacctgacatccagtaccctgatgctacagacgaggacatcacct-cacacatggaaagcgaggagttaatggt gcatacaaggc-catccccgttgcccaggacctgaacgcgccttctgattgggacagccgtgg-gaaggacagttatgaaacga gtcagctggatgaccagagtgctgaaacccacagccacaagcagtccagat-tatataagcggaaagccaatgatgagagcaa tgagcattccgatgtgattga-tagtcaggaacttccaaagtcagccgtgaattccacagccatgaatttcacagc-catgaagatat gctggttgtagaccccaaaagtaaggaagaagataaacacctgaaatttcgtat-ttctcatgaattagatagtgcatcttctgaggt caattaaaaggagaaaaaata-caatttctcactttgcatttagtcaaaagaaaaaatgctttatagcaaaat-gaaagagaacatgaa atgcttctttctcagtttattggttgaatgtgtatctatttgagtctg-gaaataactaatgtgtttgataattagtttagtttgtggcttcatg gaaactccctgtaaactaaaagcttcagggttatgtctatgttcattc-tatagaagaaatgcaaactatcactgtatttaatatttgtta ttctctcat-gaatagaaatttatgtagaagcaaacaaaatacttttacccact-taaaagagaatataacatttatgtcactataatctt ttgttttttaagttagtgtatatttgttgtgattatcttttgtggtgt-gaataaatcttttatcttgaatgtaataagaatttggtggtgtcaa ttgcttat-ttgttttccacggttgtccagcaattaataaaacataacctttt-tactgcctaaaaaaaaaaaaaaaaaa (SEQ ID NO: 4).

An exemplary coding nucleic acid sequence of human OPN-b is ctccctgtgttggtggaggatgtctgcagcagcatttaaattctgg-gagggcttggttgtcagcagcagcaggaggaggcagag cacag-catcgtcgggaccagactcgtctcaggccagttgcagccttctcagc-caaacgccgaccaaggaaaactcactaccat gagaattgcagtgatttgcttttgcctcctaggcatcacctgtgccataccagt-taaacaggctgattctggaagttctgaggaaaa gcagctttacaacaaataccca-gatgctgtggccacatggctaaacctgacc-catctcagaagcagaatctcctagccccaca gacccttccaagtaagtccaacgaaagccatgaccacatggatgatatggatgat-gaagatgatgatgaccatgtggacagcca ggactccattgactcgaacgactct-gatgatgtagatgacactgatgattctcaccagtctgatgagtctcaccattctgat gaatct gatgaactggtcactgattttcccacggacctgccagcaaccgaagttttt-cactccagttgtccccacagtagacacatatgatgg ccgaggtgatagtgtggtt-tatggactgaggtcaaaatctaagaagtttcgcagacctgacatccagtaccct-gatgctacagac gaggacatcacctcacacatggaaagcgaggagttaatggtgcatacaaggc-catccccgttgcccaggacctgaacgcgc cttctgattgggacagccgtgg-gaaggacagttatgaaacgagtcagctggatgaccagagtgctgaaacc-cacagccacaa gcagtccagattatataagcggaaagccaatgatgagagcaatgagcattcc-gatgtgattgatagtcaggaacttccaaagtc agccgtgaattccacagccat-gaatttcacagccatgaagatatgctggttgtagaccccaaaagtaaggaagaa-gataaacac ctgaaatttcgtatttctcatgaattagatagtgcatcttctgaggtcaat-taaaaggagaaaaaatacaatttctcactttgcatttagt caaaagaaaaaatgcttt-tatagcaaaatgaaagagaacatgaaatgcttctttctcagtttattggtt-gaatgtgtatctatttgagtct ggaaataactaatgtgtttgataattagtttagtttgtggcttcatg-gaaactccctgtaaactaaaagcttcagggttatgtctatgttc attc-tatagaagaaatgcaaactatcactgtatttaatatttgttattctctcat-gaatagaaatttatgtagaagcaaacaaaatacttt tacccacttaaaagagaataacattttatgtcactataatctttgttttttaagt-tagtgtatattttgttgtgattatcttttgtggtgt gaataaatcttttatctt-gaatgtaataagaatttggtggtgtcaattgcttatttgttttcc-cacggttgtccagcaattaataaaacata acctttttactgcctaaaaaaaaaaaaaaaaaa (SEQ ID NO: 5).

An exemplary coding nucleic acid sequence of human OPN-c is ctccctgtgttggtggaggatgtctgcagcagcatttaaattctgg-gagggcttggttgtcagcagcagcaggaggaggcagag cacag-catcgtcgggaccagactcgtctcaggccagttgcagccttctcagc-caaacgccgaccaaggaaaactcactaccat gagaattgcagtgatttgcttttgcctcctaggcatcacctgtgccataccagt-taaacaggctgattctggaagttctgaggaaaa gcagaatgctgtgtcctct-gaagaaaccaatgactttaaacaagagacccttccaagtaagtccaacgaaagc-catgaccacat ggatgatatggatgatgaagatgatgatgaccatgtggacagccaggactccat-tgactcgaacgactctgatgatgtagatgac actgatgattctcaccagtctgat-gagtctcaccattctgatgaatctgatgaactggtcactgattttcc-cacggacctgccagca accgaagttttcactccagttgtccccacagtagacacatatgatggccgaggtga-tagtgtggttatggactgaggtcaaaatc taagaagtttcgcagacctga-catccagtaccctgatgctacagacgaggacatcacctcacacatg-gaaagcgaggagttga atggtgcatacaaggccatccccgttgcccaggacctgaacgcgccttctgat-tgggacagccgtgggaaggacagttatgaa acgagtcagctg-gatgaccagagtgctgaaacccacagccacaagcagtccagattatataagcg-gaaagccaatgatgaga gcaatgagcattccgatgtgattgatagtcaggaacttccaaagtcagccgtgaat-tccacagccatgaatttcacagccatgaa gatatgctggttgtagaccc-caaaagtaaggaagaagataaacacctgaaatttcgtatttctcatgaattaga-tagtgcatcttctg aggtcaattaaaaggagaaaaaatacaatttctcactttgcatttagt-caaaagaaaaaatgctttatagcaaaatgaaagagaac atgaaatgcttctttctcagtttattggttgaatgtgtatctatttgagtctg-gaaataactaatgtgtttgataattagtttagtttgtggct tcatg-gaaactccctgtaaactaaaagcttcagggttatgtctatgttcattc-tatagaagaaatgcaaactatcactgtatttaatatt tgttattctctcatgaatagaaatttatgtagaagcaaacaaaatacttttacccact-taaaagagaatataacattttatgtcactata atctttgttttttaagttagtgtatat-tttgttgtgattatcttttgtggtgtgaataaatcttttatcttgaatgtaataagaat-ttggtggtg tcaattgcttatttgttttcccacggttgtccagcaattaataaaacataacctttt-tactgcctaaaaaaaaaaaaaaaaaa (SEQ ID NO: 6).

A process optionally is able to detect the expression of, expression level of (e.g. staining intensity), or positivity of one or more of OPN-a, OPN-b, and OPN-c either by histochemical staining or other suitable technique. In some aspects, immunohistochemistry (IHC) is used to detect one or more OPN variants.

Immunohistochemistry utilizes antibodies to selectively bind to a target of interest, and more particularly to an epitope present on a target of interest. The term "selectively binds" refers, with respect to an antigen such as an OPN variant, to the preferential association of an antibody or other specific binding agent, in whole or part, to the antigen and not to other antigens. Selective binding results in a relatively strong association between the binding agent (e.g., antibody) and the antigen than between the antibody and a protein that does not express an epitope for the antibody.

The binding agent is optionally coupled with a detection agent such as a fluorophore, nuclide, enzyme (e.g. horse radish peroxidase), biotin or avidin, or other suitable molecule that is capable of emitting a signal directly or following coupling with or reaction with a secondary molecule. The detection agent is an agent capable of detection, for example by spectrophotometry, flow cytometry, or microscopy. For example, one or more binding agents can be attached to an antibody, thereby permitting detection of the target protein. Optionally, one or more labels can be attached to a nucleic acid probe, thereby permitting detection of the target nucleic acid molecule. Exemplary labels include radioactive isotopes, fluorophores, ligands, chemiluminescent agents, enzymes, and combinations thereof.

The binding agent is optionally an antibody that is selective for one or more variants of OPN. Optionally, an antibody is selective for OPN-a and does not significantly cross react with either OPN-b or OPN-c or any other molecule within a sample. Optionally, an antibody is selective for OPN-b and does not significantly cross react with either OPN-a or OPN-c or any other molecule within a sample. Optionally, an antibody is selective for OPN-c and does not significantly cross react with either OPN-a or OPN-b or any other molecule within a sample. An illustrative example of an antibody that is selective for OPN-c is one that selectively binds the epitope SEEKQNAVS (SEQ ID NO: 7) or a variant thereof. Illustrative examples of such antibodies include AhOPNc that is an IgY that may be obtained from Gallus Immunotech or Exalpha Biologicals, Inc., Shirley, Mass.

In some aspects, an antibody is cross reactive between two or more OPN variants and as such may selectively detect both the presence or absence of 2 variants. Optionally, an antibody cross reacts with OPN-a and OPN-b (OPN-a/b), OPN-a and OPN-c (OPN-a/c), or OPN-b and OPN-c (OPN-b/c). Optionally an antibody is directed to OPN-a/b by recognition of an epitope selectively found on OPN-a and OPN-b that has the sequence LYNKYPDAVATWLNPDPSQKQNLLAPN (SEQ ID NO: 8). An illustrative example of an antibody that is cross reactive between OPN-a and OPN-b is LF161 available from Larry Fisher (National Institute of Dental and Craniofacial Research/NIH) or Kerafast (Boston, Mass.).

An antibody is optionally polyclonal or monoclonal. One of ordinary skill in the art understands how to produce antibodies by standard techniques and screen the resulting monoclonal or polyclonal antibodies for their ability to interact with an epitope sequence. Such methods are illustratively taught by Monoclonal Antibodies: Methods and Protocols, Albitar, M, ed., Humana Press, 2010 (ISBN 1617376469); and Antibodies: A Laboratory Manual, Harlos, E, and Lane, D. eds., Cold Spring Harbor Laboratory Press, 1988 (ISBN-10: 0879693142). Optionally, an antibody includes or is IgG, IgA, IgM, or other antibody type. A naturally occurring antibody (such as IgG, IgM, IgD) and those that result from inoculation of a mammal for production of antibodies, includes four polypeptide chains, two heavy (H) chains and two light (L) chains interconnected by disulfide bonds. As used herein, the term "antibody" also includes recombinant antibodies produced by expression of a nucleic acid that encodes one or more antibody chains in a cell (for example see U.S. Pat. Nos. 4,745,055; 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol 2:239, 1984).

The term antibody also includes an antigen binding fragment of a naturally occurring or recombinant antibody. Specific, non-limiting examples of binding fragments encompassed within the term antibody include Fab, (Fab')$_2$, Fv, and single-chain Fv (scFv) as each of these terms are recognized in the art. Methods of making these fragments are routine in the art.

The presence of the detection agent on the antibody or other specific binding agent allows a sample to be analyzed for intensity of the interaction of the OPC variant in the sample. Intensity is recognizes as the magnitude (absolute or relative) of the signal observed following selective binding to the OPC variant in the sample. Intensity is optionally detected independently for nuclei and cytoplasm. Optionally, when IHC is used the scale of detectable staining intensity is represented on a typical 1 to 3 scale to represent the intensity, wherein 0 is assigned to negative staining, 3 being assigned to very intensely staining samples, and 1 assigned to weakly staining samples. In some examples a value of 1 or 2 may be re-tested. One skilled in the art will appreciate that these values are not absolutes and the magnitude of physical staining intensity may vary depending on the samples and reagents used.

In some embodiments a process includes determining the percent positivity of a sample for the presence of one or more OPC variants. Percent positivity is optionally defined as the percentage of cells in the field or sample that show a positive result for one or more target OPC variants.

Optionally, a pathology score is assigned to each sample. A pathology score is a singular score that includes the value for intensity (e.g. 0, 1, 2, or 3), the percent positivity (on a scale of 0, 1, 2, or 3), or a combination thereof. Thus, a pathology score represents the relative value assigned to either the intensity or the percent positivity. As such one or more pathology scores are optionally included in a process.

In some embodiments a pathology score may be dichotimized into values that may be considered low (denoted L) or high (denoted H). For example, for intensity a pathology score of 0 or 1 may be categorized as L. A pathology score of 2 or 3 may be categorized as H. Similarly, for percent positivity a pathology score of 0 or 1 may be categorized as L and a pathology score of 2 or 3 may be categorized as H. Optionally, a lesion is an intermediate risk category lesion where intermediate risk is defined as one of either intensity or percent positivity being L and the other of intensity or percent positivity being H.

In some aspects, a lesion is assigned a risk category that may be based on the pathology score. For example, sine neoplasmate and ductal hyperplasia lesions may be placed in a low risk category. Flat epithelial atypia (FEA), papillomatosis intraductalis (PI), atypical ductal hyperplasia (ADH) and lobular carcinoma in situ (LCIS) may be placed into an intermediate risk category. Finally, ductal carcinoma in situ (DCIS) may be placed in a high risk category.

In some aspects, a logistic regression may be used to determine a relative risk for breast cancer in the subject based on the detection of pathology score, intensity, percent positivity, or risk category. For logical regression it is possible to use one or more of the foregoing or all four. Optionally, a ROC (receiver operating characteristic) curve can be generated as a graphical plot of sensitivity/specificity as the discrimination threshold is varied. To model outcome (survival or progression) one may use logistic regression using Formula I:

$$\pi(X_1, X_2, X_3, X_4, X_5) = \frac{e^{\beta_0+\beta_1 X_1+\beta_2 X_2+\beta_3 X_3+\beta_4 X_4+\beta_5 X_5}}{1+e^{\beta_0+\beta_1 X_1+\beta_2 X_2+\beta_3 X_3+\beta_4 X_4+\beta_5 X_5}} \quad \text{(Formula I)}$$

with X indicating the parameters measured (4 pathology scores as categorical variables and risk as a dichotomized variable) and β being the coefficient for the regression (calculated in R, a language and environment for statistical computing and graphics). The log odds are a linear function of the covariates.

Prognosing the risk of progressing to breast cancer or assessing the risk of death may be categorized as low or elevated. Optionally, the low or elevated is a relative value and dependent on the result of the pathology score and the risk category as well as either dependent on whether the pathology score is derived from the levels of intensity and/or percent positivity for OPN-a, OPN-b, OPN-c, or a combination of any of the foregoing, optionally OPN-a/b. It was found that the pathology score of OPN-c, independently when used with risk category, correlates with risk of progressing to breast cancer or risk of death such that when a sample exhibits an H for pathology score and the lesion is assigned to a high, intermediate, or low risk category, the risk of progressing to breast cancer may be prognosed as elevated. Similarly, when the pathology score in a sample is H for OPN-a/b and the lesion is assigned to a high risk category, the risk of progressing to breast cancer is prognosed as elevated. With respect to risk of death the presence of the presence of detectable OPN-c optionally independent of whether the OPN-c is of high or low intensity, of high or low percent positivity, or the use of risk category of a lesion used in the process. In other aspects a risk of death is assessed as elevated when OPN-a/b is determined to have a pathology score of H alone or in conjunction with the use of measurements specific of the intensity, percent positivity, or the use of risk category of a lesion used in the process.

Optionally, a subject is administered a treatment. A treatment is optionally correlated to a determined elevated risk of progressing to breast cancer or risk of death according to the processes as provided herein. A treatment is optionally an invasive or otherwise aggressive treatment or is a non-aggressive treatment. A non-aggressive treatment optionally includes monitoring for a predetermined or indefinite period of time. Monitoring is optionally for 1 or more years, optionally 2 or more years, optionally 5 or more years, or optionally 10 or more years. Monitoring is optionally once or more times per year. Monitoring optionally includes imaging such as MRI, mammogram, or other known monitoring method, blood screening, or other monitoring method.

In some aspects a risk of death or risk of progressing to breast cancer is considered elevated. In such circumstances a subject may be administered an intermediate or aggressive treatment. An aggressive treatment is optionally a mastectomy, a lumpectomy combined with radiotherapy and/or chemotherapy (e.g., anti-HER2, anti-ER, and/or anti-PR therapies for example Trastuzumab (Herceptin®), bevacizumab (Avastin®), pertuzumab (OmniTarg™), ZM105180 (Zemab®), ertumaxomab (Rexonum), Arimidex®, raloxifene, and tamoxifen), or an increase in the dose and/or number of courses of chemotherapy. Methods of administering such therapies are routine in the art and can be designed by skilled clinicians.

In some aspects an intermediate therapy protocol is administered. Illustrative examples of an intermediate therapy include a lumpectomy instead of a mastectomy, a lumpectomy alone instead of a lumpectomy combined with radiotherapy and/or chemotherapy, or a decrease in the dose and/or number of courses of chemotherapy. Methods of administering such therapies are routine in the art and can be designed by skilled clinicians.

Also provided are kits that may be used in one or more of the processes as provided herein. A kit optionally includes an antibody selective for OPN-c or otherwise capable of selectively binding to SEQ ID NO: 7; an antibody selective for OPN exon 4 (optionally that suitable for specifically binding to SEQ ID NO: 8); and one or more reagents for conducting an immunohistochemical analysis of a sample of a premalignant breast cancer lesion. One or more reagents for conducting immunohistochemical analysis of a sample of a premalignant breast cancer lesion optionally include antibodies, nucleic acids, or other reagents suitable for detection and optionally quantifying expression of an OPN variant. The reagent is optionally an antibody that is selective for one or more variants of OPN. Optionally, an antibody is selective for OPN-a and not significantly cross reacting with either OPN-b or OPN-c or any other molecule within a sample. Optionally, an antibody is selective for OPN-b and not significantly cross reacting with either OPN-a or OPN-c or any other molecule within a sample. Optionally, an antibody is selective for OPN-c and not significantly cross reacting with either OPN-a or OPN-b or any other molecule within a sample. An illustrative example of an antibody that is selective for OPN-c is one that selectively binds SEQ ID NO: 7 or a variant thereof. Illustrative examples of such antibodies include AhOPNc that is an IgY that may be obtained from Gallus Immunotech or Exalpha Biologicals, Inc., Shirley, Mass.

In some aspects, an antibody used in a kit as provided herein is cross reactive between two or more OPN variants and as such may selectively detect both the presence or absence of 2 variants. Optionally, an antibody cross reacts with OPN-a and OPN-b (OPN-a/b), OPN-a and OPN-c (OPN-a/c), or OPN-b and OPN-c (OPN-b/c). Optionally an antibody as provided in a kit is directed to OPN-a/b by recognition of an epitope of SEQ ID NO: 8 or a variant thereof. An illustrative example of an antibody that is cross reactive between OPN-a and OPN-b is LF161 available from Larry Fisher (National Institute of Dental and Craniofacial Research/NIH) or Kerafast (Boston, Mass.). Antibodies may be any other suitable antibody that may be prepared as described herein or as otherwise known in the art.

Specific processes, compositions and kits as described herein are illustrated in the following examples. These examples are provided for illustrative purposes and are not considered limitations on the scope of inventions.

EXPERIMENTAL

Subjects:

Biopsies from a total of 434 women with premalignant breast lesions comprising 343 patients from Wroclaw, Poland and 91 patients from Cincinnati, USA are assessed for expression of OPN-a/b or OPN-c and used for the prognostication of developing breast cancer or risk of death based on expression, pathology score alone and/or in conjunction with risk category of the lesion. The diagnoses of the lesions tested from subjects ranged from healthy breast tissue or usual ductal hyperplasia via atypia/atypical ductal hyperplasia or papillary breast lesions or LCIS to DCIS. All DCIS patients had a resection, 12 were treated with tamoxifen alone, 39 with radiation alone, and 41 with tamoxifen plus radiation therapy. The patients in Poland were followed up to 5 years, the patients in the US initially presented 2005-2011. The Cincinnati patients were not sequential specimens. Because the incidence of invasion after DCIS or atypia is very low, they were selected in two groups, those who subsequently developed invasive cancer and those who did not. The lead investigator and biostatisticians were blinded to this selection. The study was approved by the ethics committees at Wroclaw Medical University, Poland and the University of Cincinnati, USA.

Of 434 patients, 54 women had healthy breast tissue (sine neoplasmate) and 60 had usual ductal hyperplasia. These two groups are considered low risk for progression. Atypia/ADH (74 cases), papilloma/papillomatosis intraductalis (19 cases) and LCIS (20 cases) comprise an intermediate progression risk (risk of subsequent invasive cancer increases from 1.5-2.0% for proliferative lesions without atypia, to 3.5-5.0% for hyperplastic lesions with atypia (Page et al. 1985)). The 198 patients with DCIS (ductal carcinoma in situ) have an elevated risk to develop breast cancer. The risk level of radial scar is not fully characterized; 9 patients with this diagnosis were included in the overall evaluation without assignment to risk groups. Follow-up information was available for a fraction of the subjects as indicated below.

Immunohistochemistry:

Antibodies AhOPNc or LF161 were commercially obtained and used for immunohistochemical analyses of the tissue samples. For each antibody, a formalin-fixed and paraffin-embedded biopsy specimen from premalignant lesions was cut on a microtome in 5 μm slices. Antibodies were used after blocking samples in 2% donkey serum. Antibodies were diluted 1:500 to 1:700. The polyclonal rabbit antibody LF161 for staining selectively exon 4 (present in Osteopontin-a and -b) was used at 1:1000. The antibodies and their use in immunohistochemistry have been thoroughly validated (Zduniak et al. 2015 and references therein Shen/Weber 2014; Zduniak et al. 2016). For each antibody, the tissues were scored according to intensity (maximum intensity of the sample 0, 1, 2, or 3) and percent positivity (0, 1, 2, or 3), separately for nuclei and cytoplasm. In addition to analyzing the indicators in their original scale, immunohistochemical biomarkers were dichotomized into low (0-1) or high (2-3). This method was determined to strengthen the power of the analysis (Zduniak et al. 2016). All microscopic slides were independently evaluated by two pathologists, and in the rare cases of discrepant initial scores, a final score was assigned after discussion.

The anti-Osteopontin exon-4 antibody, which recognizes OPN-a and -b, stained selectively the cytoplasm. Lesions displayed OPN-c predominantly in their nuclei (lesion-free breasts had no staining). The markers (OPN-c nuclear intensity, OPN-c nuclear percent positivity, exon 4 cytoplasmic intensity, exon 4 cytoplasmic percent positivity) showed increases in average pathology scores with higher transformation risk (from low via intermediate to high). OPN-c was more stringently associated with the elevated risk groups than exon 4, reaching significant p-values for staining intensity as well as for percent positivity in all comparisons. Further, for each subgroup comparison, OPN-c staining intensity and percent positivity, but not OPN exon 4 staining, reached significant levels of difference between diagnostic entities (Table 1).

TABLE 1

Pathology Scores in Distinct Subgroups Correlate with Risk

| | | | OPNa/b intensity | percent | OPNc intensity | percent |
|---|---|---|---|---|---|---|
| low risk | intermediate risk | $\chi^2$ P | 9.635 0.022 | 5.065 0.167 | 68.385 <.0001 | 57.794 <.0001 |
| low risk | elevated risk | $\chi^2$ P | 27.600 <.0001 | 27.703 <.0001 | 129.889 <.0001 | 134.821 <.0001 |
| intermediate risk | elevated risk | $\chi^2$ P | 18.753 0.000 | 16.021 0.001 | 14.868 0.002 | 15.635 0.001 |
| SN | ADH | $\chi^2$ P | 8.313 0.040 | 12.704 0.005 | 72.489 <.0001 | 62.720 <.0001 |
| UDH | ADH | $\chi^2$ P | 8.151 0.043 | 1.752 0.625 | 19.261 0.000 | 10.382 0.016 |
| SN | DCIS | $\chi^2$ P | 48.796 <.0001 | 49.294 <.0001 | 176.546 <.0001 | 176.087 <.0001 |
| UDH | DCIS | $\chi^2$ P | 5.018 0.171 | 4.977 0.174 | 49.278 <.0001 | 54.982 <.0001 |
| ADH | DCIS | $\chi^2$ P | 15.007 0.002 | 14.304 0.003 | 15.401 0.002 | 16.015 0.001 |

Table 1 shows $\chi^2$ test for differences in pathology scores (staining intensity followed by percent positivity) among various premalignant diagnoses. P=p-value (underlined if lower than 0.05). The upper portion of the Table shows the evaluation of the main risk groups; low risk comprises SN (sine neoplasmate) and UDH (usual ductal hyperplasia); intermediate risk entails atypia/ADH (atypical ductal hyperplasia), papilloma/papillomatosis, LCIS (lobular carcinoma in situ); elevated risk is DCIS (ductal carcinoma in situ). The lower section compares pairwise the diagnostic subgroups with the largest patient numbers. OPNa/b denotes staining for exon 4, OPNc denotes staining for the splice junction of OPN-c.

Statistics:

Statistical analyses were conducted using MedCalc version 14.8.1. The pathology scores assess staining intensity and percent positivity. The predictors were each categorical or dichotomized (pathology scores 0 and 1=low versus 2 and 3=high). A second analysis included the risk group. For evaluating differences in biomarkers among the risk groups (obtained from pathology scores and the premalignant diagnoses) a $\chi^2$ test was applied. The primary methods for addressing survival time (duration) and prognosis (ensuing invasive disease or death) was Kaplan Meier for univariate analysis. A multivariate analysis of those factors with a p-value of less than 0.05 were then applied to a Cox proportional hazard model. The hazard ratio (HR) measures the hazard between two individuals, whose value of the independent variable differ by one unit (if continuous) or moving from one class to another class (for categorical variable).

Logistic Regression:

For biomarker development, ROC curves were devised using all parameters (intensity and percent positivity of the immunohistochemistry stains plus risk groups). To model outcome (survival or progression) the following formula was employed:

$$\pi(X_1, X_2, X_3, X_4, X_5) = \frac{e^{\beta_0+\beta_1 X_1+\beta_2 X_2+\beta_3 X_3+\beta_4 X_4+\beta_5 X_5}}{1+e^{\beta_0+\beta_1 X_1+\beta_2 X_2+\beta_3 X_3+\beta_4 X_4+\beta_5 X_5}}$$

with X indicating the parameters measured (4 pathology scores as categorical variables and risk as a dichotomized variable) and β being the coefficient for the regression (calculated in R, a language and environment for statistical computing and graphics). The log odds are a linear function of the covariates.

Figure 4:
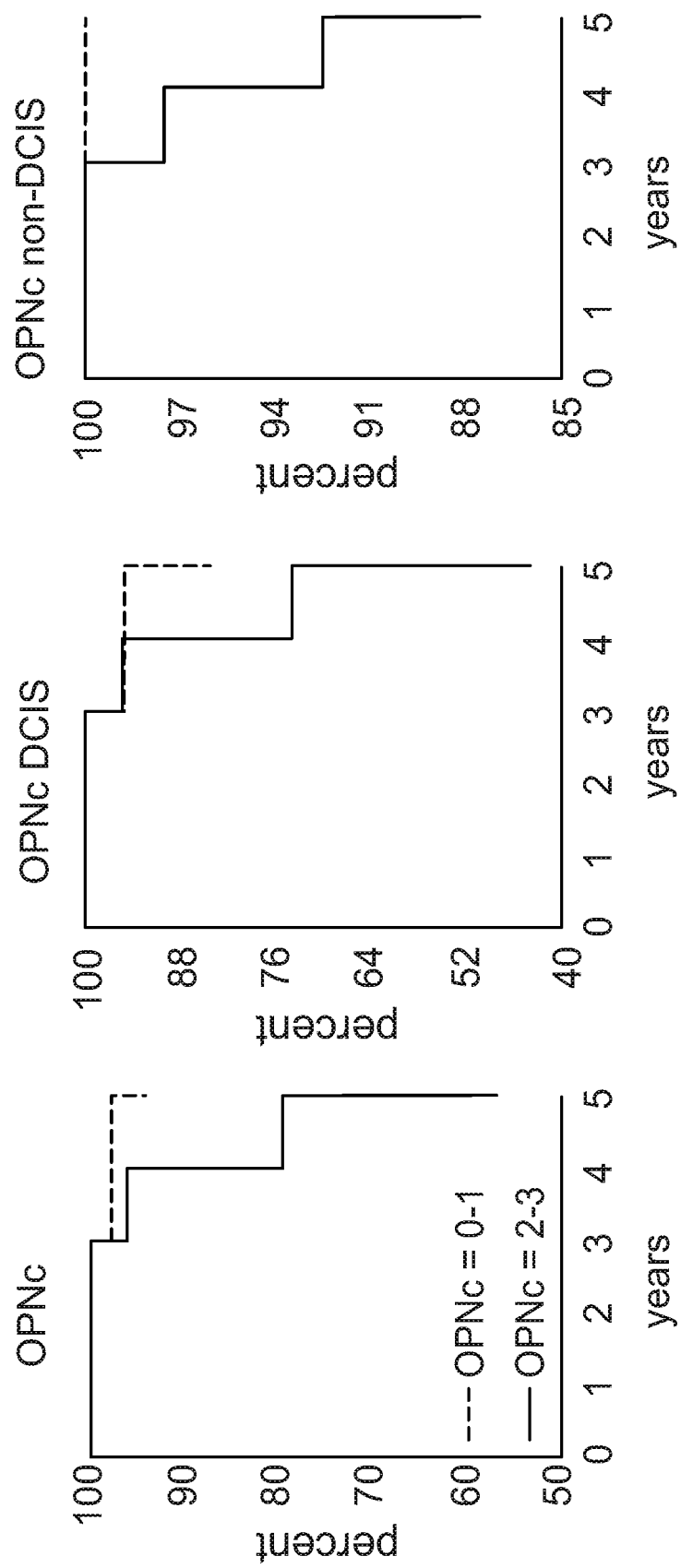
FIG. 4: illustrates survival, reflected in Kaplan-Meier Curves, prognosticated by OPN-c staining. Survival curves in relation to OPN-c staining intensity for all patients with follow-up information (left panel; N=42, 122), DCIS patients (middle panel; N=19, 82), and patients with premalignant lesions other than DCIS (right panel; N=23, 40). The change in Y-axis scale is intended to highlight the difference between OPN-c low (intensity score 0-1) and OPN-c high (intensity score 2-3), even though the risk for recurrence differs among the subgroups of patients.
Figure 5:
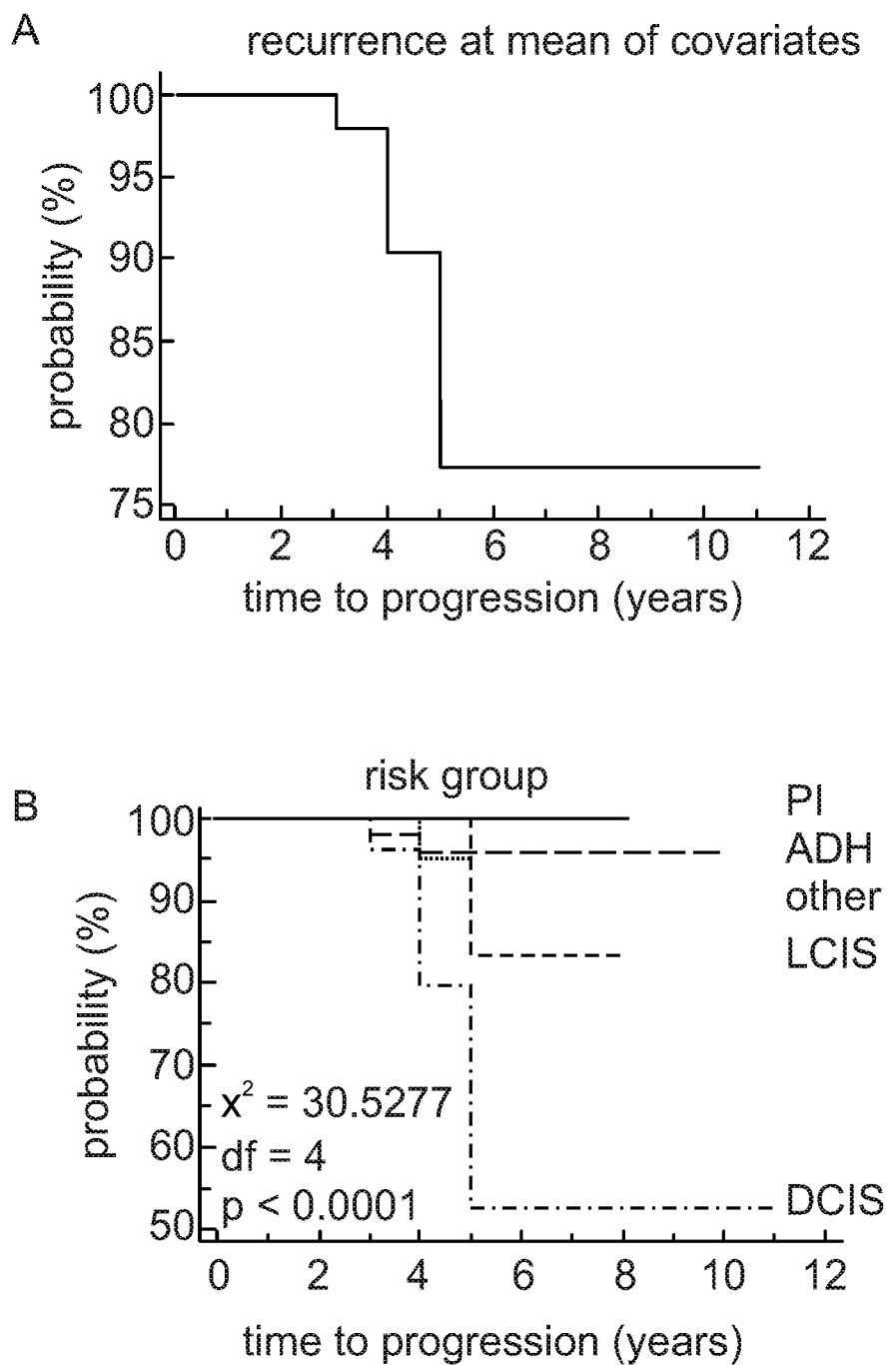
FIG. 5: illustrates multivariate analysis for the combination of prognostic indicators. A) Evaluated were the pathology scores for OPN exon 4 and OPN-c together with risk group for prognosticating recurrence. The graph represents a Kaplan-Meier curve for the risk of recurrence over time. The x-axis shows the time of follow-up in years, the y-axis displays the probability of remaining recurrence-free cases. B) Kaplan-Meier curves for the risk of recurrence over time by diagnosis. The x-axis shows the time of follow-up in years, the y-axis displays the probability of remaining progression-free cases. The measured variables are categorical. The $\chi^2$ statistic is inserted into the lower left corner of the graph, df=degrees of freedom. In both graphs, the scale of the y-axis is stretched to maximize resolution.

Prognosis:

Follow-up information had 214 patients with non-recurrence over various observation periods (111 were free of relapse for at least 5 years following the initial diagnosis) and 55 patients (20%) experiencing breast cancer over 3-5 years (48 patients had insufficient follow-up duration or died from other causes and were excluded). The data identified OPN-c intensity scores 2-3 as stronger predictors for progression than intensity scores 0-1 for all types of lesions analyzed (FIG. 4). For OPN exon 4, the probability of progression increased with score, and moderate gain was achieved by dichotomizing (FIG. 1). The dichotomized scores were used for biomarker development. Multi-variate analysis confirmed that the two biomarkers OPN-c and OPN exon 4 are prognostic for ensuing invasive disease, whereas the risk group did not add significantly to the prognostication (consistent with reports that OPN-c is a progression marker for all types of breast cancer (Mirza et al. 2008)). Among the risk groups, expectedly, DCIS was associated with the highest probability of developing breast cancer compared to PI, ADH, and LCIS (FIG. 5). A Cox proportional hazards regression model was applied for the variables under consideration. OPN-c intensity had a p-value of 0.0022 and a hazard ratio of 1.8181 (95% confidence limits 1.2427-2.6597). OPN-a/b intensity had a p-value of 0.0220 and a hazard ratio of 1.4456 (95% confidence limits 1.0564-1.9783). By contrast, the values for risk were p-value 0.7185, hazard ratio 0.9472 (95% confidence limits 0.7064-1.2702). This suggests that the OPN variant forms are biomarkers for progression hazard, also for lesions that are conventionally categorized as low risk. The markers may be of particular benefit in assessing the need for treatment in non-DCIS premalignant lesions.

Figure 2:
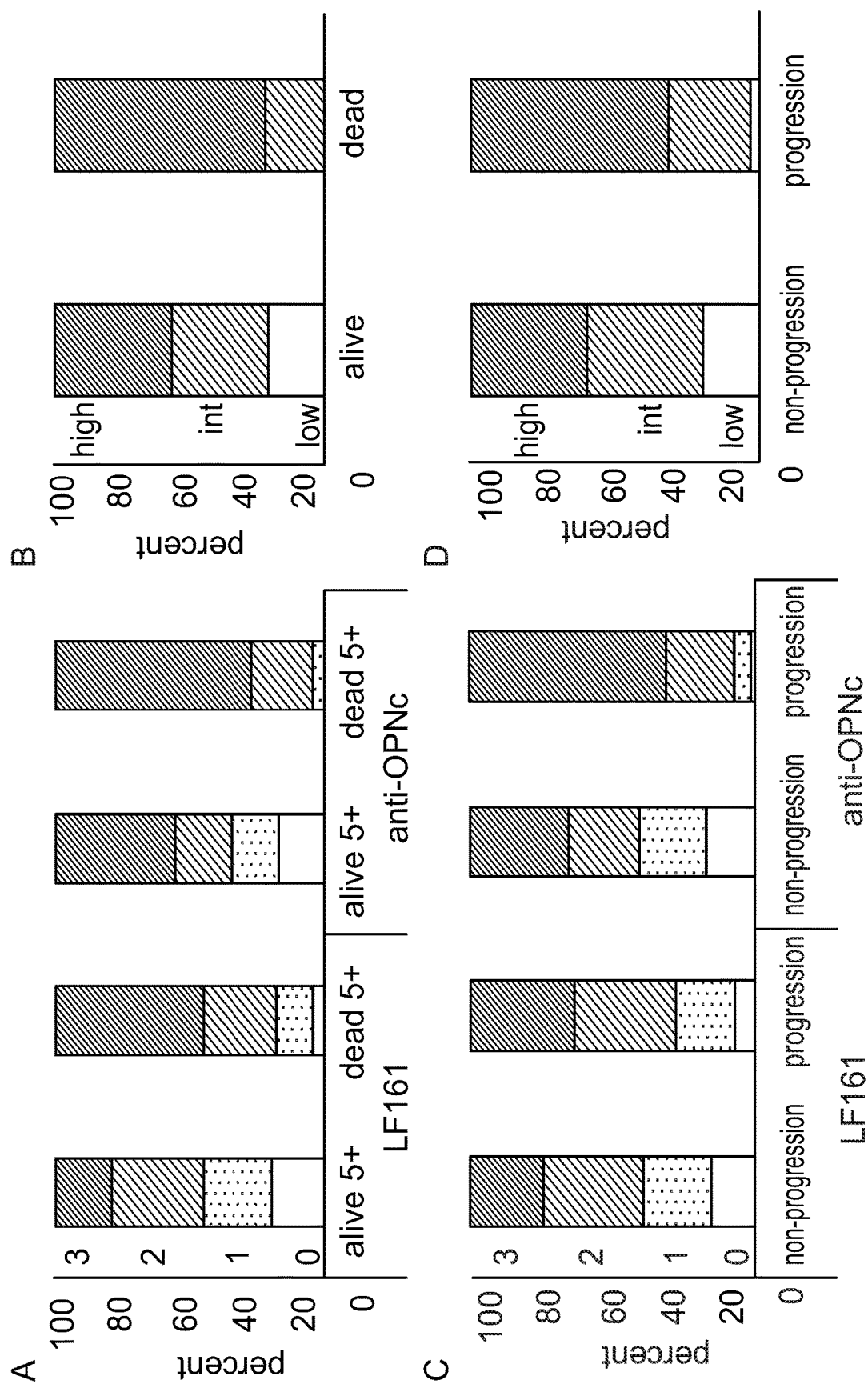
FIG. 2 illustrates that pathology scores prognosticate outcome subgroups. A,C) Shown are the distributions of pathology scores for marker staining intensity (0-3 as indicated to the left of the bars, with 0=unfilled, 1=dotted, 2=hatched, 3=filled) for 139 patients who do or do not succumb to cancer (A) and 140 patients who do or do not experience progression (C) over a time frame of 5 years (5+ indicates that some patients remained free of adverse outcome over more than 5 years, shorter follow-ups are disregarded). The left two bars reflect LF161 staining (OPN exon 4), whereas the right two bars indicate anti-OPN-c staining. The y-axis shows the number of patients as percent of the total in each group. B,D) To utilize the information of both markers and to gain discrimination, the pathology scores for OPN-c and OPN exon 4 marker intensities were combined and their distributions visualized on stacked bar graphs (low=pathology scores for both markers 0-1, intermediate=one marker 0-1 the other 2-3, high=both markers 2-3, as indicated to the left of the bars; low=unfilled, intermediate=hatched, high=filled) for patients who do or do not succumb to cancer (B) and patients who do or do not experience ensuing invasive disease (D) over a time frame of 5 years. The y-axis shows the number of patients as percent of the total in each group.

Biomarker Properties:

Patients who died from breast cancer within 5 years were evaluated in comparison to those who were alive for at least 5 years following the initial diagnosis. Analysis for the association of outcome with the markers under investigation (OPN-c, OPN exon 4) reflected them as prognostic. The pathology scores were higher for OPN exon 4 as well as for OPN-c in patients who succumbed to breast cancer compared to those who over at least 5 years did not. When combining OPN-c and OPN exon 4 staining intensity on a scale of low (pathology scores for both markers 0-1), intermediate (one marker 0-1 the other 2-3) and high (both markers 2-3), the prognostic accuracy improved such that all of the low patients were alive after 5 years, whereas women in the high category had a 30% chance to die within 5 years (with almost 20% of the survivors among them having experienced documented invasive disease). Close to 80% of patients who succumbed had a high score at the time of initial diagnosis (FIG. 2A,B). In the intermediate group, a high score for OPN-c was more unfavorable (ratio alive: dead=6.5:1) than a high score for exon 4 (ratio alive: dead=15:1).

Patients who incurred breast cancer within 5 years were evaluated in comparison to those who were free of relapse for at least 5 years following the initial diagnosis. More than 90% of women who experienced breast cancer had pathology scores of 2-3 for OPN-c intensity at the time of initial diagnosis. About 2.5% of women free of OPN-c (intensity pathology score 0), and 7.5% of OPN-c pathology score 1 progress over 5 years. This risk increases to 24% at pathology score 2 and 40% at pathology score 3. However, OPN exon 4 was less informative than OPN-c (13% at intensity score 0, 21% at score 1, 25% at score 2, 31% at score 3), so that combining the two markers yielded modest improvement over OPN-c intensity alone (FIG. 2C,D).

Figure 3:
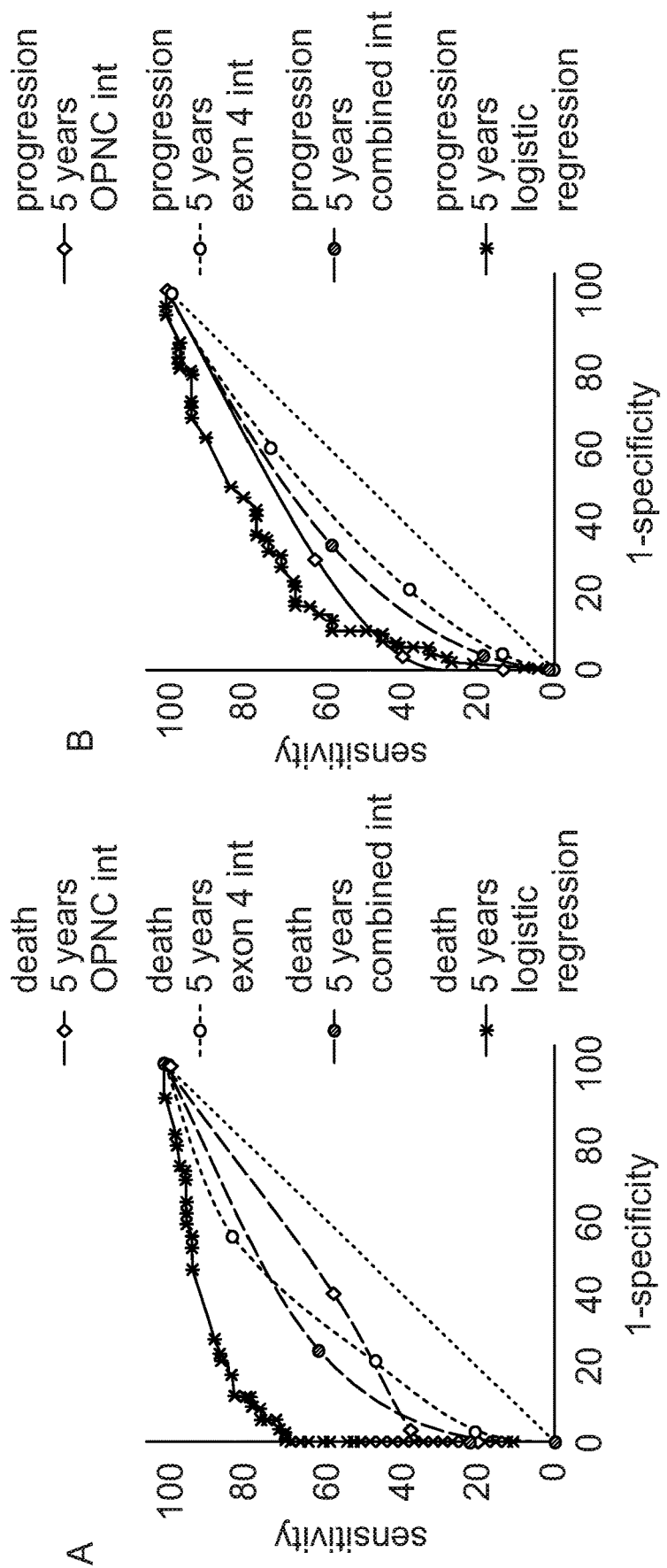
FIG. 3: illustrates that ROC curves validate the OPN splice variants as markers for progression and survival. Shown are graphs for survival (A) and progression (B). All indicators are above the diagonal. Evaluated are the pathology scores for OPN-c staining intensity alone, OPN exon 4 staining intensity alone, both markers combined, and a logistic regression analysis including all of the variables under study. The non-smooth curve-fit for the combined analysis reflects the iterations of the logistic regression as calculated in R. int=staining intensity, combined=sum of pathology scores for OPN-c and OPN exon 4 staining.

According to ROC curves, a logistic regression algorithm that applies the pathology scores as categorical variables and the dichotomized risk group (low or medium versus high) achieves better sensitivity and specificity for the prognostication of death from breast cancer (FIG. 3A) as well as for the prognostication of cancer development (FIG. 3B) than any of the individual pathology scores alone. The combined information derived from OPN-c staining, OPN exon 4 staining, and diagnosis can provide a foundation for very reliable prognostication.

Figure 6:
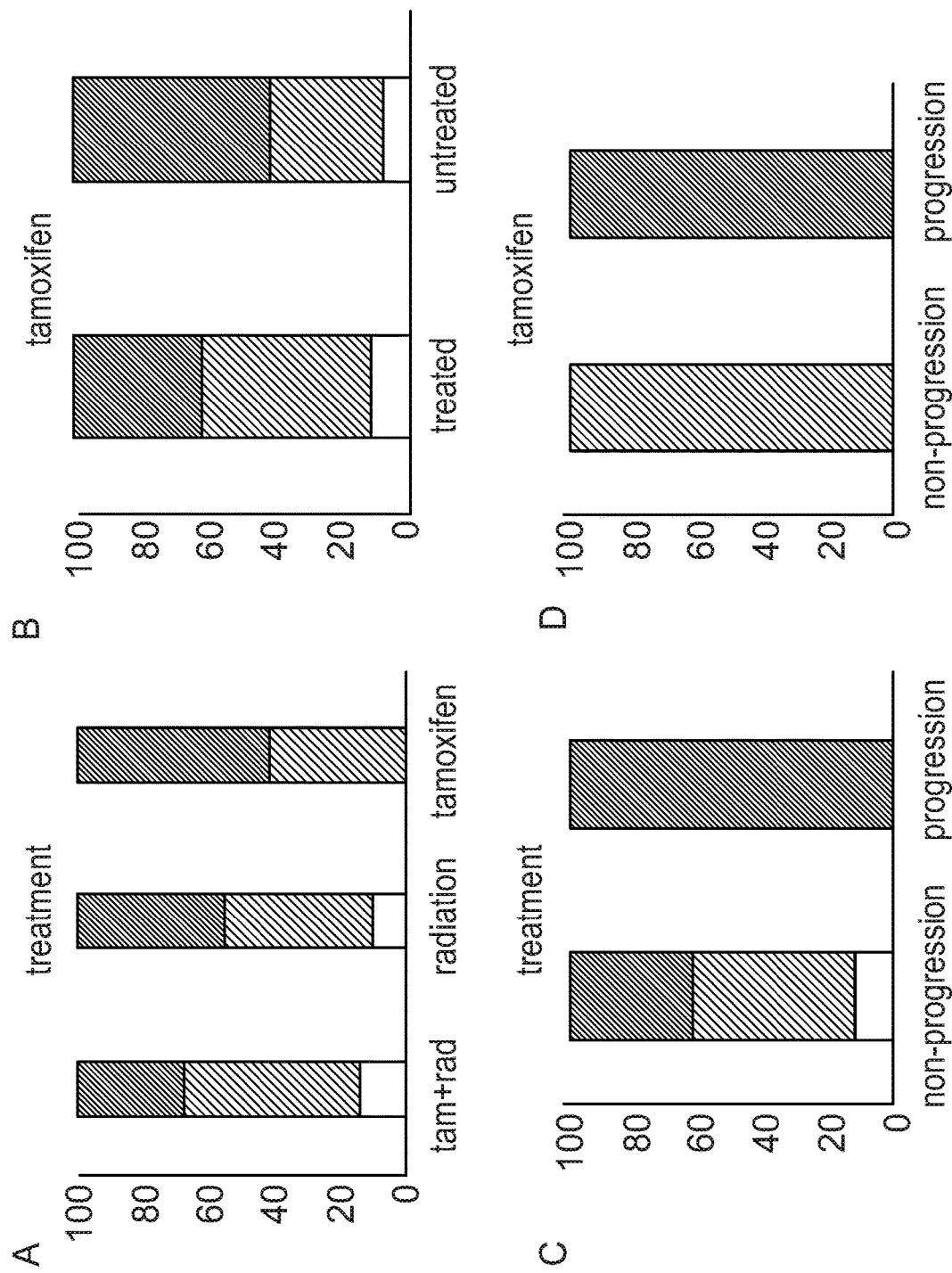
FIG. 6: illustrates DCIS outcome under treatment. Distributions of combined pathology scores for OPN-c and OPN exon 4 marker intensities (open box=low=pathology scores for both markers 0-1, hatched box=intermediate=one marker 0-1 the other 2-3, filled box=high=both markers 2-3) for patients who do or do not experience invasive disease over a time frame of 5 years. A) The distribution of combined pathology scores differs only moderately among treatment groups (tamoxifen+radiation n=41, radiation n=39, tamoxifen n=12). B) The distribution of combined pathology scores differs only moderately between tamoxifen-treated and not tamoxifen-treated patients (tamoxifen n=53, not treated n=62). C and D) Among treated patients, the combined pathology score may predict risk, but very low numbers require confirmation in a larger patient population. C) Tamoxifen and/or radiation (non-progression n=59, progression n=3). D) Tamoxifen (non-progression n=4, progression n=3).

DCIS Treatment:

All DCIS cases underwent surgical resection (16 patients had mastectomies). A fraction was further treated with tamoxifen (12), radiation (39) or both (41). While the sizes of the subgroups preclude conclusive assessments due to lack of statistical power, the trends suggest that the prognostic value of OPN-c/exon 4 is insignificantly affected by ensuing treatment, and that within each treatment group (either tamoxifen plus radiation or tamoxifen alone) the biomarker may be able to distinguish high versus low risk for invasive disease (FIG. 6).

Discussion:

Results identified OPN splice variant-c as a prognostic indicator for ensuing invasive disease and survival following premalignant breast lesions. OPN exon 4 and the diagnosis of the lesion are contributing markers. The observation is consistent with existing knowledge regarding the biological effects of the splice variants. Although the spliced OPN forms are always expressed together with the full-length form OPN-a, their ratios vary (the rate of RNA splicing is different from, and functionally independent of the rate of transcription). While OPN-a and OPN-c may synergize in tumor progression (Weber, et al., Osteopontin is a marker for cancer aggressiveness and patient survival. *Brit J Cancer* 103:861-869 (2010), OPN-c is more potent in promoting aggressive behavior (He, et al., An osteopontin splice variant induces anchorage independence in human breast cancer. *Oncogene* 25:2192-2202 (2006)). OPN splice variants have been found to be of value for breast cancer diagnosis/prognosis/prediction. Adding measurements of OPN-c and OPN exon 4 to existing diagnostic workups of precancerous lesions holds promise for assessing invasive potential and for prognosticating cancer risk, which existing markers cannot do.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Methods of producing and screening antibodies are illustratively found in Monoclonal Antibodies: Methods and Protocols, Albitar, M, ed., Humana Press, 2010 (ISBN 1617376469); and Antibodies: A Laboratory Manual, Harlos, E, and Lane, D. eds., Cold Spring Harbor Laboratory Press, 1988 (ISBN-10: 0879693142).

Additional protocols such as PCR Protocols can be found in A Guide to Methods and Applications Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," Methods in Enzymology vol. 182, and other volumes in this series; Current Protocols in Protein Science, John Wiley and Sons, New York, N.Y.; and manufacturer's literature on use of protein purification products known to those of skill in the art.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

REFERENCE LIST

Andre F, Pusztai L (2006) Molecular classification of breast cancer: implications for selection of adjuvant chemotherapy. *Nat Clin Pract Oncol* 3:621-632.

Calhoun B C, Collie A M, Lott-Limbach A A, Udoji E N, Sieck L R, Booth C N, Downs-Kelly E (2016) Lobular neoplasia diagnosed on breast Core biopsy: frequency of carcinoma on excision and implications for management. *Ann Diagn Pathol* 25:20-25.

Chivukula M, Bhargava R, Tseng G, Dabbs D J (2009) Clinicopathologic implications of "flat epithelial atypia" in core needle biopsy specimens of the breast. *Am J Clin Pathol* 131:802-808.

Cole K, Tabernero M, Anderson K S (2010) Biologic characteristics of premalignant breast disease. *Cancer Biomark* 9:177-192.

Desruisseau S, Palmari J, Giusti C, Romain S, Martin P M, Berthois Y (2005) Clinical relevance of amphiregulin and VEGF in primary breast cancers. *Int J Cancer* 111; 733-740.

Graham L J, Shupe M P, Schneble E J, Flynt F L, Clemenshaw M N, Kirkpatrick A D, Gallagher C, Nissan A, Henry L, Stojadinovic A, Peoples G E, Shumway N M (2014) Current approaches and challenges in monitoring treatment responses in breast cancer. *J Cancer* 5:58-68.

Hartmann L C, Radisky D C, Frost M H, Santen R J, Vierkant R A, Benetti L L, Tarabishy Y, Ghosh K, Visscher D W, Degnim A C (2014) Understanding the premalignant potential of atypical hyperplasia through its natural history: a longitudinal cohort study. *Cancer Prev Res* 7:211-217.

Hartung F, Weber G F (2013) RNA blood levels of osteopontin splice variants are cancer markers. *SpringerPlus* 2:110.

He B, Mirza M, Weber G F (2006) An osteopontin splice variant induces anchorage independence in human breast cancer. *Oncogene* 25:2192-2202.

Henry N L, Hayes D F (2006) Uses and abuses of tumor markers in the diagnosis, monitoring, and treatment of primary and metastatic breast cancer. *Oncologist* 11:541-552.

Kleer C G, Cao Q, Varambally S, Shen R, Ota I, Tomlins S A, Ghosh D, Sewalt R G, Otte A P, Hayes D F, Sabel M S, Livant D, Weiss S J, Rubin M A, Chinnaiyan A M (2003) EZH2 is a marker of aggressive breast cancer and promotes neoplastic transformation of breast epithelial cells. *Proc Natl Acad Sci USA* 100:11606-11611.

Mirza M, Shaughnessy E, Hurley J K, Vanpatten K A, Pestano G A, He B, Weber G F (2008) Osteopontin-c is a selective marker for breast cancer. *Int J Cancer* 122:889-897.

Ortiz-Martinez F, Perez-Balaguer A, Ciprián D, Andrés L, Ponce J, Adrover E, Sánchez-Payá J, Aranda F I, Lerma E, Perió G (2014) Association of increased osteopontin and splice variant-c mRNA expression with HER2 and triple-negative/basal-like breast carcinomas subtypes and recurrence. *Hum Pathol* 45:504-512.

Page D L, Dupont W D, Rogers L W, Rados M S (1985) Atypical hyperplastic lesions of the female breast. A long-term follow-up study. *Cancer* 55:2698-2708.

Pang H, Lu H, Song H, Meng Q, Zhao Y, Liu N, Lan F, Liu Y, Yan S, Dong X, Cai L (2013) Prognostic values of osteopontin-c, E-cadherin and β-catenin in breast cancer. *Cancer Epidemiol* 37:985-992.

Patani N, Jiang W, Mokbel K (2008a) Osteopontin C mRNA expression is associated with a poor clinical outcome in human breast cancer. *Int J Cancer* 122:2646.

Patani N, Jouhra F, Jiang W, Mokbel K (2008b) Osteopontin expression profiles predict pathological and clinical outcome in breast cancer. *Anticancer Res* 28:4105-4110.

Said S M, Visscher D W, Nassar A, Frank R D, Vierkant R A, Frost M H, Ghosh K, Radisky D C, Hartmann L C, Degnim A C (2015) Flat epithelial atypia and risk of breast cancer: A Mayo cohort study. *Cancer* 121:1548-1555.

Santisteban M, Reynolds C, Barr Fritcher E G, Frost M H, Vierkant R A, Anderson S S, Degnim A C, Visscher D W, Pankratz V S, Hartmann L C (2010) Ki67: a time-varying biomarker of risk of breast cancer in atypical hyperplasia. *Breast Cancer Res Treat* 121:431-437.

Schnitt S J (2003) The diagnosis and management of pre-invasive breast disease: flat epithelial atypia—classification, pathologic features and clinical significance. *Breast Cancer Res* 5:263-268.

Shen H, Weber G F (2014) The osteopontin-c splice junction is important for anchorage-independent growth. *Mol Carcinog* 53:480-487.

Weber G F (2008) Molecular mechanisms of metastasis. *Cancer Letters* 270:181-190.

Weber G F (2016) Metabolism in cancer metastasis. *Int J Cancer* 138:2061-2066.

Weber G F, Lett G S, Haubein N C (2010) Osteopontin is a marker for cancer aggressiveness and patient survival. *Brit J Cancer* 103:861-869.

Weber G F, Lett G S, Haubein N C (2011) Categorical meta-analysis of Osteopontin as a clinical cancer marker. *Oncol Reports* 25:433-441.

Zduniak K, Agrawal A, Agrawal S, Hossain M M, Ziolkowski P, Weber G F (2016) Osteopontin splice variants are differential predictors of breast cancer treatment responses. *BMC Cancer* 16:441.

Zduniak K, Ziolkowski P, Ahlin C, Agrawal A, Agrawal S, Blomqvist C, Fjällskog M L, Weber G F (2015) Nuclear osteopontin-c is a prognostic breast cancer marker. *Brit J Cancer* 112:729-738.

U.S. Patent Application Publication 2018/0119232

Patents, applications, and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A method for prognosing an elevated risk in a patient diagnosed with a premalignant lesion of the breast, of the lesion progressing to breast cancer and treating the patient, the method comprising:
   providing a sample of the premalignant lesion;
   detecting one or more variants of Osteopontin (OPN) selected from OPN-a, OPN-b, and OPN-c in the sample, wherein detecting comprises immunohistochemically staining the sample and measuring one or more of stain intensity and percent positivity for each stain;
   assigning a pathology score to the sample, the pathology score comprising 0, 1, 2, or 3 for stain intensity, or 0, 1, 2, or 3 for stain percent positivity;
   dichotomizing the pathology score into low (L=0 or 1) or high (H=2 or 3);
   assigning the premalignant lesion to a risk category based on lesion type, wherein sine neoplasmate and ductal hyperplasia lesions comprise a low risk category, flat epithelial atypia (FEA), papillomatosis intraductalis (PI), atypical ductal hyperplasia (ADH), and lobular carcinoma in situ (LCIS) comprise an intermediate risk category, and ductal carcinoma in situ (DCIS) comprises a high risk category;
   prognosing an elevated risk of the lesion progressing to breast cancer when:
      (a) OPN-c is detected, the sample having a pathology score of H and the lesion having a risk category of low, intermediate, or high; and/or
      (b) OPN-a or OPN-b is detected, the sample having a pathology score of H and the lesion having a risk category of high; and
   administering chemoprevention therapy or surgery to the patient prognosed with the elevated risk of the lesion progressing to breast cancer.

2. The method according to claim 1, wherein the sample is selected from a nucleic sample, a cytoplasmic sample, or both.

3. The method according to claim 2, wherein immunohistochemically staining comprises contacting the sample with at least one antibody selective for one or more variants of OPN.

4. The method according to claim 3, wherein at least one antibody selectively stains OPN-c (anti-OPN-c), and at least one antibody selectively stains OPN-a and/or OPN-b (anti-OPN-a/b).

5. The method according to claim 4, wherein the antibody selective for OPN-c selectively binds an epitope comprising the sequence SEEKQNAVS (SEQ ID NO: 7) or a variant thereof, and/or the antibody selective for OPN-a/b binds an epitope comprising the sequence LYNKYPDA-VATWLNPDPSQKQNLLAPN (SEQ ID NO: 8) or a variant thereof.

6. The method according to claim 5, wherein the antibody comprises IgY AhOPNc or LF161.

7. The method according to claim 1 wherein the step of prognosing comprises subjecting a staining intensity or percent positivity of an immunohistochemistry stain for OPN-a/b and OPN-c, and risk category to a logistic regression to thereby determine risk for breast cancer or for death from breast cancer.

8. The method according to claim 1, wherein chemoprevention therapy is selected from one or both of administering at least one estrogen receptor modulator and radiation.

9. The method according to claim 8, wherein the estrogen receptor modulator is selected from raloxifene and tamoxifen.

10. A method of assessing an elevated risk of death from breast cancer in a patient diagnosed with a premalignant lesion of the breast and treating the patient, the method comprising:
providing a sample of the premalignant lesion;
immunohistochemically detecting OPN-a, OPN-b and/or OPN-c in the sample by detecting selective anti-OPN-c and anti-OPN-a/b stains and measuring one or more of intensity and percent positivity for each stain;
assigning a pathology score for each stain, comprising scoring the stains 0, 1, 2, or 3 for intensity and 0, 1, 2, or 3 for percent positivity and classifying the pathology score for each stain as high (H=2 or 3), low (L=0 or 1), or intermediate (I=one L and one H);
assigning the premalignant lesion to a risk category based on lesion type, wherein sine neoplasmate and ductal hyperplasia lesions comprise a low risk category, flat epithelial atypia (FEA), papillomatosis intraductalis (PI), atypical ductal hyperplasia (ADH), and lobular carcinoma in situ (LCIS) comprise an intermediate risk category, and ductal carcinoma in situ (DCIS) comprises a high risk category;
assessing the risk of death as elevated when:
(a) OPN-c is detected, the sample having a pathology score of H or I and the lesion having a risk category of high, intermediate, or low; or
(b) OPN-a/b is detected, the sample having a pathology score of H and the lesion having a risk category of high or intermediate, or
(c) OPN-a/b is detected, the sample having a pathology score of H or I and the lesion having a risk category of high; and
administering chemoprevention therapy or surgery to the patient assessed with the elevated risk of death from breast cancer.

11. The method according to claim 10, further comprising assessing the risk of death as elevated when OPN-a/b is detected with a pathology score of H.

12. The method according to claim 10, further comprising assessing the risk of death as elevated when OPN-c is detected with a pathology score of H.

13. The method according to claim 10, wherein chemoprevention therapy is selected from one or both of administering at least one estrogen receptor modulator and radiation.

14. The method according to claim 13, wherein chemoprevention therapy is selected from one or both of administering at least one estrogen receptor modulator and radiation.

* * * * *